United States Patent

Ondetti et al.

[11] 3,976,660
[45] Aug. 24, 1976

[54] PYRROLIDINE DERIVATIVES

[75] Inventors: Miguel Angel Ondetti, Princeton; Edward Condon, Trenton, both of N.J.

[73] Assignee: E. R. Squibb & Sons, Inc., Princeton, N.J.

[22] Filed: Aug. 15, 1974

[21] Appl. No.: 497,799

[52] U.S. Cl.................. 260/326.43; 260/326.46; 260/326.5 R; 424/274
[51] Int. Cl.².................................. C07D 207/28
[58] Field of Search....... 260/326.2, 326.43, 326.46, 260/326.5 R

[56] References Cited
UNITED STATES PATENTS
3,285,931  11/1966  Huisgen..................... 260/326.2 X OTHER PUBLICATIONS
Chem. Abs., 1952, vol. 48, p. 11436.

*Primary Examiner*—Dale R. Ore
*Attorney, Agent, or Firm*—Lawrence S. Levinson; Merle J. Smith

[57] ABSTRACT

Pyrrolidine derivatives which have the formula

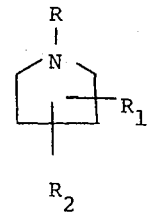

wherein R and $R_1$ each is hydrogen, —$(CH_2)_6COOH$, —$(CH_2)_6COO$— lower alkyl, or —$(CH_2)_6COO$ benzyl and $R_2$ is hydrogen, —CO—O—$(CH_2)_5CH_3$, —CO—NH—$(CH_2)_5CH_3$ —$(CH_2)_7CH_3$ or —CH=CH—CH(OH)—$(CH_2)_4$—$CH_3$, at least one of R and $R_1$ is hydrogen and $R_1$ and $R_2$ are not both hydrogen, are new compounds which are useful as inhibitors of prostaglandin dehydrogenase and as potentiators of prostaglandin activity.

20 Claims, No Drawings

PYRROLIDINE DERIVATIVES

SUMMARY OF THE INVENTION

This invention relates to new pyrrolidine derivatives which are useful as inhibitors of prostaglandin dehydrogenase and potentiators of prostaglandin activity. They have the formula (I)

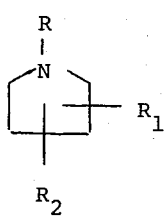

R and $R_1$ each is hydrogen, $-(CH_2)_6COOH$ or the lower alkyl ester or benzyl ester of the latter. The lower alkyl group is a straight or branched chain hydrocarbon radical having one to seven carbon atoms like methyl, ethyl, propyl, isopropyl, butyl and the like. The one to four carbon straight chain radicals are preferred, especially methyl.

$R_2$ is hydrogen or one of the eight membered chains $-CO-O-(CH_2)_5CH_3$, $-CO-NH-(CH_2)_5CH_3$, $-(CH_2)_7CH_3$ or $-CH=CH-CH(OH)-(CH_2)_4-CH_3$.

In any individual compound of the group, at least one of the substituents represented by R and $R_1$ is hydrogen and at least one of the substituents represented by $R_1$ and $R_2$ is other than hydrogen. In other words, at least one of the long chain groups represented by R, $R_1$ or $R_2$ is present, but not more than two of these long chain groups are present and, when two long chain groups are present, they are different, one being selected from the R and $R_1$ groups and the other being selected from the $R_2$ groups.

R and $R_1$ are preferably the acid form $-(CH_2)_6COOH$. The groups represented by R and $R_1$ can be on the nitrogen or on any carbon in the ring. The groups represented by $R_2$ can be on any carbon in the ring. If there are two long chain substituents on the pyrrolidine ring, i.e., either R or $R_1$ is other than hydrogen and $R_2$ is also other than hydrogen, then the two chain substituents are preferably attached to adjacent members of the ring.

DETAILED DESCRIPTION OF THE INVENTION

The new pyrrolidine derivatives of this invention are inhibitors of a 15α-hydroxy prostaglandin dehydrogenase which is an enzyme inactivating prostaglandin. These new compounds are therefore useful to potentiate or to extend the useful life of prostaglandins such as prostaglandin E which is a vasodilator (hypotensive) agent, a gastric antisecretory agent and a bronchodilator. See Coutinho, Prostaglandins II: Clinical Aspects (MSS Info. Corp., N.Y.; 1973), pp41–53; Cuthbert, The Prostaglandins (Lippincott Co., Phila.); 1973. They are administered intravenously, or intramuscularly, before or preferably, in conjunction with the prostaglandin at a dosage of 5 to 50 mg./kg. Depending on the particular application, the dose of prostaglandin E varies from 50 to 500 micrograms/kg. The ratio of potentiator to prostaglandin is approximately about 50 to 500:1.

The new compounds of this invention are formulated alone or in conjunction with the prostaglandin by dissolving or suspending in a sterile vehicle for injection, preferably water, according to conventional pharmaceutical practice. A dosage unit containing about 100 to 500 mg. of the active substance of this invention per unit of volume is appropriate for formulation.

The new pyrrolidine derivatives of this invention are produced from pyrrolidine carboxylic acids, i.e., proline, 3-pyrrolidinecarboxylic acid or their $R_1$ substituted derivatives.

The compounds of formula I having one side chain, i.e., those wherein R and $R_1$ are both hydrogen and $R_2$ is other than hydrogen, are produced by first protecting the nitrogen of proline or 3-pyrrolidinecarboxylic acid, e.g., with a carbobenzoxy group or a t-butoxycarbonyl group by conventional procedure.

The $R_2$ group is then introduced by reaction of the appropriate derivative with the carboxyl group of the protected proline or 3-pyrrolidinecarboxylic acid, e.g., in an inert organic solvent such as dimethylformamide or tetrahydrofuran. The protecting group is then removed by hydrogenolysis, e.g., in the presence of palladium-carbon, or by treatment with acid, e.g., trifluoroacetic acid.

However, a preferred procedure for producing octylpyrrolidine is by reduction of 5-octyl-2-pyrrolidinone using lithium aluminum hydride in a medium such as tetrahydrofuran. The 5-octyl-2-pyrrolidinone is obtained by treatment of methyl-4-oxodecanoate with ammonium bromide and sodium cyanoborohydride.

Also, a preferred procedure for producing (3-hydroxy-1-octenyl)pyrrolidine is by reduction of N-protected-(3-oxo-1-octenyl)pyrrolidine, the nitrogen being protected by a butyloxycarbonyl group, and removing the protecting group with trifluoroacetic acid. The N-protected-(3-oxo-1-octenyl)pyrrolidine is obtained from N-protected-pyrrolidinecarboxaldehyde which is reacted with an alkyl 2-oxoheptylphosphonate like dimethyl 2-oxoheptylphosphonate and sodium hydride in a medium like dimethoxyethane.

In those compounds of formula I with two side chains, i.e., when $R_1$ and $R_2$ are both other than hydrogen, the disubstituted compound can be obtained from the $R_2$-mono-substituted compounds described above by alkylation of the nitrogen with the appropriate alkyl halide, e.g., with benzyl 7-iodoheptanoate, or an $R_1$-substituted pyrrolidine-carboxylic acid is first formed and the $R_2$ group is introduced as described above.

The $R_1$-substituted pyrrolidinecarboxylic acids are produced by cyclizing a compound of one of the following formulas

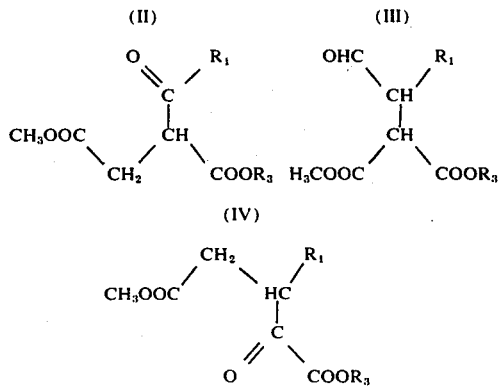

$R_3$ is one of the protecting groups described above. This is effected by reductive alkylation with ammonium bromide, lactamization, and reduction of the resulting pyrrolidine with triethyloxonium fluoroborate and sodium borohydride. The nitrogen on the resulting pyrrolidinecarboxylic acid is then protected and the compound is subjected to the same series of reactions described above.

Additional details of these reactions are found in the examples.

The compounds of this invention can be isolated as free bases, as zwitterions, or as their acid addition salts. They form acid addition salts with a variety of inorganic and organic acids providing such salts as the hydrohalides, e.g., hydrochloride, hydrobromide, etc., sulfate, nitrate, borate, phosphate, maleate, oxalate, citrate, etc. The physiologically acceptable salts, especially the maleic acid salt, are preferred. The acid addition salts frequently provide a convenient means for isolating the product, e.g., by forming and precipitating the salt in an appropriate menstruum in which the salt is insoluble. If another salt is desired or the salt used for isolation is not physiologically acceptable, then, after separation of the first salt, the free base can be obtained by neutralization with a common base and the desired new salt is obtained by reaction with the appropriate acid.

Certain products of this invention, particularly those derived from starting materials like proline, occur in stereoisomeric forms. The various stereoisomeric forms as well as racemic mixtures thereof are included within the scope of this invention.

The examples which follow constitute preferred embodiments. They also illustrate how other members of the group are produced by appropriate variations in the reactants. All temperatures are in degrees celsius.

EXAMPLE 1

2-[(Hexyloxy)carbonyl]pyrrolidine

A. To a stirred solution of 24.9 g. (0.01 mol.) of N-carbobenzoxy-DL-proline and 11.22 g. (0.11 mol.) of n-hexanol in 200 ml. of dry dimethylformamide and 7.9 g. pyridine at room temperature is added 20.6 g. (0.01 mol.) of N,N'-dicyclohexylcarbodiimide. After stirring this mixture at room temperature for 16 hours, the precipitated N,N'-dicyclohexylurea is filtered off, the filtrate is diluted with a large volume of saturated aqueous sodium chloride, and this is thoroughly extracted with chloroform. The combined extracts are dried and concentrated in vacuo to give an oil comprising 1-(benzyloxy)carbonyl)]-2-[(hexyloxy)carbonyl]-pyrrolidine.

B. The oil is dissolved in 250 ml. of methanol and hydrogenolyzed in the presence of 2.5 g. of 5% palladium/carbon. The catalyst is filtered off, and the filtrate is concentrated in vacuo to give 2-[(hexyloxy)-carbonyl]pyrrolidine.

EXAMPLE 2

2-[(Hexylamino)carbonyl]pyrrolidine

A. To a solution of 25.9 g. (0.07 mol.) of N-carbobenzoxy-DL-proline p-nitrophenyl ester in 250 ml. of dry tetrahydrofuran is added 14.1 g. (0.140 mol.) of n-hexylamine in 50 ml. of tetrahydrofuran, and the resulting solution is left overnight at room temperature. The solvent is removed in vacuo, the residue is diluted with ether, and this solution is then washed thoroughly with 1 N aqueous sodium hydroxide, water and then dilute hydrochloric acid. On drying the ether solution and concentrating in vacuo, a pale yellow oil comprising 1-[(benzyloxy)carbonyl]-2-[(hexylamino)carbonyl]pyrrolidine is obtained.

B. A solution of the oil in 500 ml. of methanol is hydrogenolyzed in the presence of 2.27 g. of 5% palladium/carbon. The catalyst is filtered off, the filtrate is concentrated in vacuo, and the residue dissolved in ethyl acetate. The ethyl acetate solution is thoroughly extracted with dilute hydrochloric acid, the combined extracts are made basic with 1N aqueous sodium hydroxide, and this is thoroughly extracted with ether. The combined extracts are dried and concentrated in vacuo to give 2-[(hexylamino)carbonyl]-pyrrolidine. The oily residue is dissolved in a minimum amount of ether and is mixed with a warm alcoholic solution of one equivalent of oxalic acid. The crystalline oxalate precipitates upon cooling, m.p. 128°-129°. By substituting a warm alcoholic solution of maleic acid, a crystalline maleic acid addition salt separates on cooling, m.p. 61°-64°.

When N-carbobenzoxy-L-proline is used as starting material, the L-oxalate is obtained, m.p. 150°-151°.

EXAMPLE 3

2-Octylpyrrolidine

A. 4-Oxododecanoic acid [A. Takeda et al., J. Org. Chem. 31, 616 (1966)] is converted into its methyl ester by the method of R. O. Clinton and S. C. Laskowski, J. Am. Chem. Soc., 70, 3135 (1948).

B. A solution of 6.84 g. (0.030 mol.) of methyl-4-oxododecanoate, 15.0 g. (0.150 mol.) of ammonium bromide and 3.80 g. (0.060 mol.) of sodium cyanoborohydride is stirred at room temperature for 5 days [method of R. F. Borch, et al., J. Am. Chem. Soc. 93, 2897 (1971)]. Concentrated hydrochloric acid is added to the solution until a pH of 2 is obtained. The methanol is removed in vacuo, the residue is taken up in water, and this is thoroughly extracted with ether. The ether extracts are dried and concentrated in vacuo to an oil comprising 5-octyl-2-pyrrolidone which is used without further purification.

C. A solution of the oil obtained in part B in 100 ml. of dry tetrahydrofuran is added dropwise to a stirred suspension of lithium aluminum hydride (4 equivalents) in 200 ml. of dry tetrahydrofuran. The stirred suspension is then refluxed overnight under nitrogen. The reaction mixture is cooled and the excess lithium aluminum hydride is decomposed by careful addition of saturated aqueous sodium sulfate. The tetrahydrofuran is removed in vacuo, the residue is taken up in dilute hydrochloric acid, and this solution is extracted with ether. The aqueous acid solution is made basic with 1 N aqueous sodium hydroxide and thoroughly extracted with ether. The combined ether extracts are dried and concentrated in vacuo to give 2-octylpyrrolidine.

EXAMPLE 4

2-(3-Hydroxy-1-octenyl)pyrrolidine

A. To a stirred solution of 21.6 g. (0.10 mol.) of N-t-butoxycarbonyl-DL-proline in 100 ml. of dry tetrahydrofuran at room temperature is added 50 ml. of a 1 molar diborane solution in tetrahydrofuran at such a rate that the temperature of the reaction mixture is maintained at 25°–30°. After the addition is complete, the reaction mixture is stirred at room temperature for an additional hour. Water is then cautiously added to the reaction mixture, the tetrahydrofuran is removed in vacuo, the residue is diluted with ether, and this solution is washed thoroughly with 5% aqueous sodium hydroxide. The ether solution is dried and concentrated in vacuo to obtain 1-(t-butoxycarbonyl)-2-pyrrolidinemethanol.

B. Chromium trioxide-pyridine complex is prepared in situ in methylene chloride by the method of R. Ratcliffe and R. Rodehorst, J. Org. Chem., 35, 4000 (1970). To this reagent (0.60 mol., 5% solution in methylene chloride) is added in one portion a solution of 20.2 g. (0.10 mol.) of the reduction product from part A. After stirring the mixture for 15 minutes at room temperature, the methylene chloride solution is decanted from the tarry black precipitate, washed with 5% aqueous sodium hydroxide, 5% hydrochloric acid saturated with sodium chloride, dried, and concentrated in vacuo. The 1-(t-butoxycarbonyl)-2-pyrrolidinecarboxaldehyde thus obtained is used immediately without further purification.

C. A solution of 15.0 g. (0.075 mol.) of the aldehyde from part B in 200 ml. of dimethoxyethane is added to a previously prepared mixture of 25.0 g. (0.113 mol.) of dimethyl 2-oxo-heptylphosphonate and 4.58 g. (0.109 mol.) of 57% sodium hydride mineral oil dispersion in 450 ml. of dry dimethoxyethane. The mixture is stirred at room temperature under nitrogen for one hour, then poured into water and thoroughly extracted with ether. The ether is washed with water, saturated aqueous sodium chloride, dried, and concentrated in vacuo to give crude 1-(t-butoxycarbonyl)-2-(3-oxo-1-octenyl)pyrrolidine.

D. The material obtained in part C is dissolved in 250 ml. of anhydrous dimethoxyethane and treated with 150 ml. of a 1 M solution of zinc borohydride [J. J. Pappas, et al., Tet. Let., 4273 (1966)] in dimethoxyethane at 0° for 8 hours. The excess reagent is destroyed with a saturated solution of sodium potassium tartrate. The reaction mixture is poured into water and extracted with ethyl acetate. The extract is washed with water and saturated aqueous sodium chloride solution, dried and concentrated in vacuo to obtain 1-(t-butoxycarbonyl)-2-(3-hydroxy-1-octenyl)-pyrrolidine.

E. The residue from part D is dissolved in 50 ml. of trifluoroacetic acid at 0° and left to stand for 3 hours at 0°. The trifluoroacetic acid is removed in vacuo, the residue is taken up in chloroform, washed with 5% aqueous sodium bicarbonate, saturated aqueous sodium chloride, dried, and concentrated in vacuo to give 2-(3-hydroxy-1-octenyl)-pyrrolidine.

EXAMPLE 5

2-[(Hexyloxy)carbonyl]-1-pyrrolidineheptanoic acid

A. A solution of 1.99 g. (0.01 mol.) of 2-[(hexyloxy)-carbonyl]pyrrolidine obtained in Example 1, 3.45 g. (0.01 mol.) of benzyl 7-iodoheptanoate and 1.21 g. (0.012 mol.) of triethylamine in 10 ml. of benzene is heated at 50° for 16 hours. The cooled reaction mixture is washed with 5% aqueous sodium bicarbonate, saturated aqueous chloride, dried, and concentrated in vacuo to give an oil, 2-[(hexyloxy)carbonyl]-1-pyrrolidineheptanoic acid benzyl ester.

B. The oil obtained in part A is dissolved in 5 ml. of glacial acetic acid and hydrogenated in the presence of 0.25 g. of 5% palladium/carbon. The catalyst is filtered off, and the filtrate is concentrated in vacuo to give 2-[(hexyloxy)carbonyl]-1-pyrrolidine heptanoic acid.

EXAMPLE 6

2-[(Hexylamino)carbonyl]-1-pyrrolidineheptanoic acid

By substituting the 2-[(hexylamino)carbonyl]-pyrrolidine, obtained in Example 2, for the 2-[(hexyloxy)-carbonyl]pyrrolidine in the procedure of Example 5, 2-[(hexylamino)carbonyl]-1-pyrrolidineheptanoic acid is obtained.

The methyl ester of this compound, isolated as the maleate salt, melts at 61°–62°.

EXAMPLE 7

2-Octyl-1-pyrrolidineheptanoic acid

By substituting the 2-octylpyrrolidine obtained in Example 3 for the 2-[(hexyloxy)carbonyl]pyrrolidine in the procedure of Example 5, 2-octyl-1-pyrrolidineheptanoic acid is obtained.

EXAMPLE 8

2-(3-Hydroxy-1-octenyl)-1-pyrrolidineheptanoic acid

The 2-(3-hydroxy-1-octenyl)pyrrolidine obtained in Example 4 is alkylated with benzyl 7-iodoheptanoate by the procedure described in Example 5. A solution of the crude product in aqueous tetrahydrofuran is stored overnight with 1.1 equivalents of sodium hydroxide. The tetrahydrofuran is removed in vacuo and the aqueous solution is extracted with ether. The pH of the aqueous solution is adjusted to 7 with dilute aqueous sodium hydroxide, and the solution is concentrated in vacuo. Gel filtration chromatography (Sephadex LH-20-methanol) of the residue yields 2-(3-hydroxy-1-octenyl-1-pyrrolidineheptanoic acid.

EXAMPLE 9

1-Pyrrolidineheptanoic acid

By substituting pyrrolidine for the 2-[(hexyloxy)carbonyl]pyrrolidine in the procedure of Example 5, 1-pyrrolidineheptanoic acid is obtained.

EXAMPLE 10

3-Carboxy-1-phenylmethyloxycarbonylpyrrolidine

A solution of 205 g. (1 mol.) of N-benzylpyrrolidine 3-carboxylic acid (CA 64, 14173d) is dissolved in glacial acetic acid (1 l.) and hydrogenated in the presence of 40 g. of 10% palladium on charcoal until no more starting material is detected by TLC. The catalyst is filtered off and the filtrate is concentrated to dryness in vacuo. The residue is treated with benzyloxycarbonyl chloride by a Schotten-Baumann reaction to obtain 3-carboxy-1-phenylmethyloxycarbonylpyrrolidine.

EXAMPLE 11

3-[(Hexyloxy)carbonyl]pyrrolidine

By substituting the 3-carboxy-1-phenylmethyloxycarbonylpyrrolidine obtained in Example 10 for the 2-[(hexyloxy)carbonyl]pyrrolidine in the procedure of Example 1, 3-[(hexyloxy)carbonyl]pyrrolidine is obtained.

EXAMPLE 12

3-[(Hexylamino)carbonyl]pyrrolidine

By substituting the 3-carboxy-1-phenylmethyloxycarbonylpyrrolidine obtained in Example 10 for the N-carbobenzoxy-DL-proline p-nitrophenyl ester in the procedure of Example 2, 3-[(hexylamino)carbonyl]pyrrolidine is obtained.

EXAMPLE 13

1-(t-Butyloxycarbonyl)-3-pyrrolidinecarboxylic acid

A solution of 205 g. (1 mol.) of N-benzylpyrrolidine-3-carboxylic acid (CA, 64 14173d) is dissolved in glacial acetic acid (1 l.) and hydrogenated in the presence of 40 g. of 10% palladium on charcoal until no more starting material is detected by TLC. The catalyst is filtered off and the filtrate is concentrated to dryness in vacuo. The residual 3-pyrrolidine carboxylic acid is dissolved in a mixture of DMF-H$_2$O (2:1) (2 liters), triethylamine (1 mol.), t-butoxycarbonyl azide (1.5 mol.) is added and the mixture is stirred at room temperature for two days. Periodically the pH is tested with pH paper, and after twenty-four hours more azide (0.5 mol.) is added. The solvent is concentrated in vacuo to remove the DMF, the aqueous phase is acidified with citric acid (to pH 2-3) and extracted with ethyl acetate. The organic phase is concentrated to dryness in vacuo to yield the product 1-(t-butyloxycarbonyl)-3-pyrrolidinecarboxylic acid.

EXAMPLE 14

3-(3-Hydroxy-1-octenyl)pyrrolidine

By substituting 3-carboxy-1-t-butyloxycarbonylpyrrolidine for the N-t-butoxycarbonyl-DL-proline in the procedure of Example 4, 3-(3-hydroxy-1-octenyl)pyrrolidine is obtained.

EXAMPLE 15

3-Octylpyrrolidine 3-octylpyrrolidine is prepared by starting from 1-(t-butyloxycarbonyl)-3-pyrrolidinecarboxylic acid (Example 13) and following the steps A and B of the procedure of Example 4. Then step C is carried out as follows:

C. A mixture of 0.15 mol. of anhydrous sodium iodide and 150 ml. of dry methyl ethyl ketone is heated for 30 minutes at 80°, 0.1 mol of 1-chloroheptane is added, and heating is continued for 10 hours with periodic shaking. The cooled solution is filtered and most of the solvent is distilled off. The residue is diluted with 150 ml. of benzene, the solution is washed with water, 5% sodium thiosulfate, water, and dried over magnesium sulfate. The filtrate solution is concentrated to 100 ml., 0.12 mol. of triphenyl phosphine is added and the mixture is heated for 10 hours at 80°. The benzene is distilled off and the residue is triturated with ether, filtered and dried. A solution of 25 mmoles of this heptyltriphenyl phosphonium iodide in 40 ml. of dried DMF is mixed rapidly with 20 mmoles of sodium methoxide and the mixture is stirred for one hour at room temperature. The solution of heptylidenetriphenyl phosphorane is cooled with ice water and mixed with a solution of the 15 mmoles of the 1-(t-butoxycarbonyl)-3-pyrrolidinecarboxaldehyde obtained in step B, dissolved in 10 ml. of DMF and the mixture is stirred at 20° for 20 hours. After dilution with water, the desired 1-(t-butoxycarbonyl)-3-(1-octenyl)pyrrolidine is extracted with ethyl acetate. The ethyl acetate extract is concentrated to dryness in vacuo and the residue is hydrogenated in the presence of 10% palladium on charcoal, then treated with trifluoroacetic acid as in step E of the same example to obtain 3-octylpyrrolidine.

EXAMPLE 16

2-Pyrrolidineheptanoic acid

2-Pyrrolidineheptanoic acid is prepared from N-t-butoxycarbonylproline following steps A and B of Example 4 and step C of the procedure of Example 15. In step C, benzyl ω-chlorohexanoate is substituted for the 1-chloroheptane. The product thus obtained is hydrogenated in the presence of 10% palladium on charcoal and is then treated with trifluoroacetic acid, as in step E of the same procedure.

EXAMPLE 17

3-(t-Butyloxycarbonyl)-2-pyrrolidineheptanoic acid phenylmethyl ester

A. A stirred suspension of 59 g. (0.75 g-atom) of activated zinc in 500 ml. of dry tetrahydrofuran containing a crystal of iodine is brought to reflux under nitrogen. To this is added slowly a solution of 12.1 g. (0.50 mol.) of benzyl 7-formylheptanoate and 117 g. (0.60 mol.) of t-butyl bromoacetate in 500 ml. of dry tetrahydrofuran. Within a few minutes, the solution becomes cloudy and the iodine color disappears, indicating that the reaction has started. After the addition is complete (30 minutes), the mixture is stirred and refluxed for an additional hour. The cooled solution is then poured into 0.1 N hydrochloric acid and the pH adjusted to 2 with 2 N hydrochloric acid. The excess zinc is filtered off and the filtrate thoroughly extracted with ethyl acetate. The combined extracts are dried and concentrated in vacuo to give crude 3-hydroxydecanedioic acid 10-benzyl ester-1-t-butyl ester.

A solution of the above product in methylene chloride is oxidized with chromium trioxide-pyridine complex as described in Example 4, step B to obtain 3-oxodecanedioic acid 10-benzyl ester-1-t-butyl ester.

B. 16.9 g. (0.40 mol.) of a 57% sodium hydride-mineral oil dispersion is freed from mineral oil by washing with hexane under an atmosphere of nitrogen and covered with 100 ml. of dry dimethoxyethane. To this stirred suspension is added dropwise a solution of 125 g. (0.40 mol.) of the ester obtained in part A in 200 ml. of dimethoxyethane containing 0.02 moles of t-butanol. The mixture is then refluxed under nitrogen for two hours and cooled to room temperature. To this stirred suspension is added dropwise a solution of 75 g. (0.45 mol.) of ethyl bromoacetate in 150 ml. of dimethoxyethanol. After refluxing the mixture for 1 hour, it is cooled to 0°-5°, and dilute hydrochloric acid is added. The layers are separated, the organic layer is washed with saturated aqueous sodium chloride, dried, and concentrated in vacuo.

C. The product from step B is subjected to reductive alkylation-cyclization as described is step B of Example 3 to obtain 3-(t-butyloxycarbonyl)-(2-pyrrolidin-5-one)heptanoic acid phenylmethyl ester.

D. The product from step C is reduced by the method of R. F. Borch, Tet. Let., 61 (1968). Thus, a solution of triethyloxonium fluoroborate (13.28 g., 70 mmoles) and 26.20 g. (65 mmoles) of the product from step C in 50 ml. of dry methylene chloride is stirred for twenty-four hours at room temperature. The methylene chloride is removed in vacuo, and the residue is dissolved in 75 ml. of absolute ethanol. To this stirred solution is added 6.0 g. (158 mmoles) of sodium borohydride in portions, and when the addition is complete, stirring is continued for twenty-four hours at room temperature. The solution is poured into water and thoroughly extracted with ether. The combined ether extracts are washed with saturated aqueous sodium chloride, dried, and concentrated in vacuo to obtain 3-t-butyloxycarbonyl-2-pyrrolidineheptanoic acid phenylmethyl ester.

EXAMPLE 18

3-Carboxy-1-[(phenylmethyloxy)carbonyl]-2-pyrrolidineheptanoic acid phenylmethyl ester The product of Example 17 (0.1 mol.) is added to a mixture of dichloromethane (200 ml.), triethylamine (0.11 mol.) and benzyloxycarbonyl chloride. The mixture is stirred for 2 hours at room temperature, washed with 5% potassium bisulfate, water, dried, and concentrated to dryness. The residue, 3-(t-butoxycarbonyl)-1-[(phenylmethyloxy)carbonyl]-2-pyrrolidineheptanoic acid phenylmethyl ester is dissolved in trifluoroacetic acid and the solution stored at room temperature for 1 hour. The solution is concentrated to dryness in vacuo yielding 3-carboxy-1-[(phenylmethyloxy)carbonyl]-2-pyrrolidineheptanoic acid phenylmethyl ester.

EXAMPLE 19

3-](Hexyloxy)carbonyl]-2-pyrrolidineheptanoic acid

By substituting 3-carboxy-1-[(phenylmethyloxy)carbonyl]-2-pyrrolidineheptanoic acid phenylmethyl ester (Example 18) for the N-carbobenzoxy-DL-proline in the procedure of Example 1, 3-[(hexyloxy)carbonyl]-2-pyrrolidineheptanoic acid is obtained.

EXAMPLE 20

3-[(Hexylamino)carbonyl]-2-pyrrolidineheptanoic acid

By substituting 3-carboxy-1-[(phenylmethyloxy)carbonyl]-2-pyrrolidineheptanoic acid phenylmethyl ester in the procedure of Example 2, 3-[(hexylamino)carbonyl]-2-pyrrolidineheptanoic acid is obtained.

EXAMPLE 21

3-Carboxy-1-[(t-butyloxy)carbonyl]-2-pyrrolidineheptanoic acid phenylmethyl ester The product of Example 17 is dissolved in trifluoroacetic acid and the solution is stored at room temperature for one hour. The mixture is then concentrated to dryness in vacuo, and the residue is acylated with t-butyloxycarbonyl azide by the procedure described in Example 13 to obtain 3-carboxy-1-[(t-butyloxy)carbonyl]-2-pyrrolidineheptanoic acid phenylmethyl ester.

EXAMPLE 22

3-(3-Hydroxy-1-octenyl)-2-pyrrolidineheptanoic acid

By substituting 3-carboxy-1-[(t-butyloxy)carbonyl]-2-pyrrolidineheptanoic acid phenylmethyl ester in the procedure of Example 4, steps A, B, C and D, saponifying the product thus obtained by the procedure of Example 8, and then removing the t-butyloxycarbonyl group with trifluoroacetic acid as described in Example 18, 3-(3-hydroxy-1-octenyl)-2-pyrrolidineheptanoic acid is obtained.

EXAMPLE 23

3-Octyl-2-pyrrolidineheptanoic acid

By substituting 3-carboxy-1-[(t-butyloxy)carbonyl]-2-pyrrolidineheptanoic acid phenylmethyl ester (Example 21) in the procedure of Example 15, 3-octyl-2-pyrrolidineheptanoic acid is obtained.

EXAMPLE 24

3-Pyrrolidineheptanoic acid

The product 3-pyrrolidineheptanoic acid is prepared from N-t-butyloxycarbonylpyrrolidine 3-carboxylic acid (Example 13), following the procedure of Example 16.

EXAMPLE 25

4-[(t-Butyloxy)carbonyl]-3-pyrrolidineheptanoic acid phenylmethyl ester

A. The pyrrolidine enamine of benzyl-8-formyloctanoate is prepared by the method of Stork et al., [J. Am. Chem. Soc., 85, 207 (1963)]. To a solution of 154.5 g. (0.5 mol.) of this enamine in dry dioxane (500 ml.), 1.45 g. (0.55 mol.) of 1-t-butyl-2-bromo-3-methylmalonate is added and the resulting mixture is refluxed for 12 hours. Water (100 ml.) is added and the refluxing is continued for one more hour. The dioxane is removed in vacuo, the residue is taken up in ether and washed with 5% potassium bisulfate, 5% aqueous sodium carbonate, water, dried, and concentrated to dryness in vacuo to obtain 2-(methoxy- carbonyl)-3-formyldecanedioic acid 10-benzyl ester-1-t-butyl ester.

B. The product obtained in the preceding step is subjected to reductive alkylation-cyclization as described in step B of Example 3 to obtain 4-(t-butyloxy)-carbonyl-(3-pyrrolidine-5-one)heptanoic acid phenylmethyl ester.

C. The product obtained in the preceding step is reduced by the procedure of step D, Example 17 to obtain 4-[(t-butyloxy)carbonyl]-3-pyrrolidineheptanoic acid phenylmethyl ester.

EXAMPLE 25

4-Carboxy-1-[(phenylmethyloxy)carbonyl]-3-pyrrolidineheptanoic acid

The product 4-carboxy-1-[(phenylmethyloxy)carbonyl]-3-pyrrolidineheptanoic acid is prepared by the procedure of Example 18, starting with the 4-[(t-butyloxy)carbonyl]-3-pyrrolidineheptanoic acid phenylmethyl ester obtained in Example 25.

EXAMPLE 27

4-[(Hexyloxy)carbonyl]-3-pyrrolidineheptanoic acid

The product 4-[(hexyloxy)carbonyl]-3-pyrrolidineheptanoic acid is prepared starting with the acid of Exampl 26, and following the procedure described in Example 1.

EXAMPLE 28

4-[(Hexylamino)carbonyl]-3-pyrrolidineheptanoic acid

The product 4-[(hexylamino)carbonyl]-3-pyrrolidineheptanoic acid is prepared starting with the acid of Example 26, and following the procedure described in Example 2.

EXAMPLE 29

4-Carboxy-1-[(t-butyloxy)carbonyl]-3-pyrrolidineheptanoic acid phenylmethyl ester The product 4-carboxy-1-[(t-butyloxy)carbonyl]-3-pyrrolidineheptanoic acid phenylmethyl ester is prepared starting with the product of Example 25, and following the procedure of Example 21.

EXAMPLE 30

4-(3-Hydroxy-1-octenyl)-3-pyrrolidineheptanoic acid

The product 4-(3-hydroxy-1-octenyl)-3-pyrrolidineheptanoic acid is prepared starting with the product obtained in Example 29, and following the procedure of Example 22.

EXAMPLE 31

4-Octyl-3-pyrrolidineheptanoic acid

The product 4-octyl-3-pyrrolidineheptanoic acid is prepared starting with the product obtained in Example 29 and following the procedure of Example 15.

EXAMPLE 32

2-[(t-Butyloxy)carbonyl]-3-pyrrolidineheptanoic acid phenylmethyl ester

A. 16.9 g. (0.4 mol.) of a 57% sodium hydride mineral oil dispersion is freed from mineral oil by washing with hexane under an atmosphere of nitrogen and covered with 100 ml. of dry dimethoxyethane. To his stirred suspension is added dropwise a solution of 86 g. (0.4 mol.) of 1-t-butyl-2-oxo-5-methylglutarate in dimethoxyethane (200 ml.) containing 0.02 moles of t-butanol. The mixture is then refluxed under nitrogen for two hours and cooled to room temperature. A solution of 180 g. (0.45 mol.) of 1-benzyl-7-iodoheptanoate in 150 ml. of dimethoxyethane is added dropwise and the mixture is refluxed for another hour. After cooling to 0°–5° dilute hydrochloric acid is added. The layers are separated and the organic phase is washed with brine, dried, and concentrated to dryness in vacuo to obtain 3-(methoxycarbonylmethyl)-2-oxodecanedioic acid 10-benzyl ester-1-t-butyl ester.

B. The ketone obtained in the preceding step is subjected to reductive alkylation-cyclization as described in step B of Example 3, and reduced to 2-[(t-butyloxy)-carbonyl]-3-pyrrolidineheptanoic acid phenylmethyl ester.

EXAMPLE 33

2-Carboxy-1-[(phenylmethyloxy)carbonyl]-3-pyrrolidineheptanoic acid phenylmethyl ester The product 2-carboxy-1-[(phenylmethoxyloxy)carbonyl]-3-pyrrolidineheptanoic acid phenylmethyl ester is prepared from the product obtained in Example 32, by the procedure described in Example 18.

EXAMPLE 34

2-[(Hexyloxy)carbonyl]-3-pyrrolidineheptanoic acid

The product 2-[(hexyloxy)carbonyl]-3-pyrrolidineheptanoic acid is prepared starting from the product of Example 33, by the procedure of Example 1.

EXAMPLE 35

2-[(Hexylamino)carbonyl]-3-pyrrolidinepheptanoic acid

The product 2-[(hexylamino)carbonyl]-3-pyrrolidineheptanoic acid is prepared starting from the product of Example 33, by the procedure of Example 2.

EXAMPLE 36

2-Carboxy-1-[(t-butyloxy)carbonyl]-3-pyrrolidineheptanoic acid phenylmethyl ester The product 2-carboxy-1-[(t-butyloxy)carbonyl]-3-pyrrolidineheptanoic acid phenylmethyl ester is prepared starting from the product of Example 32, by the procedure of Example 21.

EXAMPLE 37

2-(3-Hydroxy-1-octenyl)-3-pyrrolidineheptanoic acid

The product 2-(3-hydroxy-1-octenyl)-3-pyrrolidineheptanoic acid is prepared starting from the product of Example 35, by the procedure of Example 22.

EXAMPLE 38

2-Octyl-3-pyrrolidineheptanoic acid

The product 2octyl-3-pyrrolidineheptanoic acid is prepared starting from the product of Example 35, by the procedure of Example 15.

EXAMPLE 39

1-t-Butyl-2-bromo-3-methylmalonate 1-t-Butyl-2-bromo-3-methylmalonate is prepared by bromination of 1-methyl-3-t-butylmalonate [C. R. Hauser, et al., J. Chem. Soc., 68, 27 (1946) ] by the procedure described by C. Kremer, et al., [J. Am. Chem. Soc., 64, 1010 (1942) ].

EXAMPLE 40

7-Iodoheptanoic acid phenylmethyl ester

Benzyl hydrogen pimelate is prepared from pimelic acid by the procedure of Organic Synthesis, Coll. Vol. II, p. 276 for preparing ethyl hydrogen sebacate.

Benzyl hydrogen pimelate is reduced to benzyl 7-hydroxyheptanoate with diborane in tetrahydrofuran by the method described in Example 4, step A.

To a solution of 147 g. (0.624 mol.) of benzyl 7-hydroxyheptanoate in 1 l. of dry pyridine at 0° is added 143 g. (0.749 mol., 1.2 equiv.) of p-toluenesulfonyl chloride, and the mixture stirred until all solid is in solution (15 minutes). This solution is kept at 0° for 48 hours. Most of the pyridine is removed in vacuo, the residue is added to ice water and thoroughly extracted with ether. The combined ether extracts are washed with dilute hydrochloric acid, dried, and concentrated in vacuo to give the crude tosylate of benzyl 7-hydroxyheptanoate.

The tosylate (16.5 g. 0.424 mol.) is stirred overnight in the dark with 127 g. (0.848 mol.) of sodium iodide in 1.25 l. of acetone. The sodium tosylate is filtered off, washed with acetone and the filtrate is concentrated in vacuo. The residue is dissolved in ether, extracted with water, aqueous sodium bisulfite, dried and concentrated in vacuo to give 7-iodoheptanoic acid phenylmethyl ester.

EXAMPLE 41

6-Formylheptanoic acid phenylmethyl ester

Benzyl hydrogen sebacate is prepared from sebacic acid by the procedure of Organic Syntheses, Coll. Vol. II, p. 276, for preparing ethyl hydrogen sebacate.

Benzyl hydrogen sebacate is reduced to benzyl 8-hydroxyoctanoate with diborane in tetrahydrofuran by the method described in Example 4, step A.

Benzyl 8-hydroxyoctanoate is oxidized to benzyl 7-formylheptanoate by Collins oxidation as described in Example 4, step B.

EXAMPLE 42

1-t-Butyl-2-oxo-5-methylglutarate

γ-Methylglutarate (10 mmoles), cupric chloride (5 mmoles) and pyridoxal hydrochloride (10 mmoles) are dissolved in water and the pH of the solution is adjusted to 5. Water is added to a volume of 200 ml. and the solution is heated in a boiling water bath for 1.5 hours. The solution is chilled, the pH is adjusted to 6.5 and the solution applied to a sulfonic acid ion exchange column (Dowex 50-X 8) in the hydrogen form. The fractions containing the keto acid are pooled, concentrated to dryness and the residue is dissolved in a mixture of methylene chloride (100 ml.), liquid isobutylene (50 ml.), and concentrated sulfuric acid (0.1 ml.). The mixture is stirred in a pressure jar for three days. The isobutylene is allowed to evaporate at room temperature, the organic phase is washed with saturated sodium bicarbonate, water, dried, and the solvent is removed in vacuo to obtain 1-t-butyl-2-keto-5-methylglutarate.

EXAMPLE 43

Conversion of Acids to Methyl Esters

The acids of Examples 5, 6, 7, 8, 9, 14, 16, 19, 20, 22, 23, 24, 27, 28, 30, 31, 34, 35, 37 and 38 are converted to their corresponding methyl esters by dissolution in methanol and addition of an ethereal solution of diazomethane until there is a persistent yellow color, then the solution is concentrated to obtain the product.

What is claimed is:

1. A compound of the formula

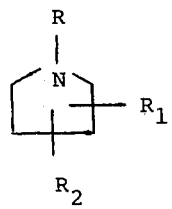

wherein R and $R_1$ each is hydrogen, $-(CH_2)_6COOH$, $-(CH_2)_6COO$—lower alkyl or $-(CH_2)_6COO$-benzyl; and $R_2$ is hydrogen, $-COO-(CH_2)_5CH_3$, $-CO-NH-(CH_2)_5CH_3$, $-(CH_2)_7CH_3$ or $-CH=CH-CH(OH)-(CH_2)_4CH_3$, with the proviso that at least one of R and $R_1$ is hydrogen, and at least one of the substituents represented by $R_1$ and $R_2$ is other than hydrogen and at least one of the long chain groups represented by $R_1$ R, or $R_2$ is present but not more than two of these long chain groups are present and physiologically acceptable acid addition salts thereof.

2. A compound as in claim 1 wherein R is $-(CH_2)_6COOH$.

3. A compound as in claim 1 wherein $R_1$ is $-(CH_2)_6COOH$.

4. A compound as in claim 1 wherein $R_2$ is $-CO-NH-(CH_2)_5CH_3$.

5. A compound as in claim 1 wherein $R_2$ is $-COO-(CH_2)_5CH_3$.

6. A compound as in claim 2 wherein $R_2$ is $-(CH_2)_7CH_3$.

7. A compound as in claim 1 wherein $R_2$ is $-CH=CH-CH(OH)-(CH_2)_4CH_3$.

8. A compound as in claim 4 wherein R and $R_1$ each is hydrogen.

9. A compound as in claim 8 wherein the compound is 2-[(hexylamino)carbonyl]pyrrolidine.

10. A compound as in claim 4 wherein R is $-(CH_2)_6COOH$ and $R_1$ is hydrogen.

11. A compound as in claim 10 wherein the compound is 2-[(hexylamino)carbonyl]-1-pyrrolidineheptanoic acid.

12. A compound as in claim 1 having two long chain substituents attached to adjacent members of the ring said substituents are different, one being selected from the R and $R_1$ groups and the other being selected from the $R_2$ group.

13. A compound as in claim 2 wherein $R_2$ is 2—COO—$(CH_2)_5CH_3$.

14. A compound as in claim 2 wherein $R_2$ is 2—CH=CH—CH(OH)—$(CH_2)_4CH_3$.

15. A compound as in claim 3 wherein R, is 2—$(CH_2)_6COOH$ and $R_2$ is 3—COO—$(CH_2)_5CH_3$.

16. A compound as in claim 3 wherein R, is 2—$(CH_2)_6COOH$ and $R_2$ is 3—CO—NH—$(CH_2)_5CH_3$.

17. A compound as in claim 3 wherein R, is 2—$(CH_2)_6COOH$ and $R_2$ is 3—CH=CH—CH(OH)—$(CH_2)_4CH_3$.

18. A compound as in claim 1 wherein R is $-(CH_2)_6$COO-lower alkyl.

19. A compound as in claim 1 wherein R is $-(CH_2)_6$COO-benzyl.

20. A compound as in claim 3 wherein $R_1$ is 3—$(CH_2)_6COOH$ and $R_2$ is 4—CO—NH—$(CH_2)_5CH_3$.

* * * * *